United States Patent [19]

Opie

[11] 4,207,266

[45] Jun. 10, 1980

[54] PROCESS FOR THE PREPARATION OF TRIFLUOROMETHYLATED AROMATIC COMPOUNDS

[75] Inventor: Thomas R. Opie, Collingswood, N.J.

[73] Assignee: Rohm and Haas Company, Philadelphia, Pa.

[21] Appl. No.: 19,060

[22] Filed: Mar. 9, 1979

[51] Int. Cl.$^2$ .............................................. C07C 85/14
[52] U.S. Cl. ........................ 260/651 F; 260/651 HA; 260/192; 568/16; 568/35; 568/34; 568/56; 568/65; 568/316; 568/929; 568/937; 568/936; 568/655; 568/656; 562/495; 562/493; 562/496; 556/476
[58] Field of Search ...................... 260/651 F, 651 HA

[56] References Cited

U.S. PATENT DOCUMENTS

| | | | |
|---|---|---|---|
| 2,273,922 | 7/1940 | Benning et al. | 260/649 |
| 3,950,445 | 4/1976 | Ryf | 260/651 F |
| 4,157,344 | 6/1979 | Feiring | 260/575 |

OTHER PUBLICATIONS

Giles et al., *Trans. Far. Soc.* 62, 128, (1966).
Tiers, *JACS*, 82, 5513 (1960).
Kobayaski et al., *Tetrahedron Let.*, 4095 (1969).
Hasek et al., *JACS*, 82, 543 (1960).

*Primary Examiner*—C. Davis

[57] ABSTRACT

This invention relates to a novel process for the direct trifluoromethylation of aromatic compounds via carbon tetrachloride and hydrogen fluoride in the presence of strong Bronsted or Lewis acids which give an acidic reaction (increase in concentration of $H_2F^+$ ions) in anhydrous hydrogen fluoride.

14 Claims, No Drawings

PROCESS FOR THE PREPARATION OF TRIFLUOROMETHYLATED AROMATIC COMPOUNDS

BACKGROUND OF THE INVENTION

Trifluoromethylated aromatic compounds are important intermediates for the production of several commercially important herbicides including triflualin-fluometuronnorflurazon. Trifluoromethyl substituted compounds are utilized in other areas as well.

The preparation of trifluoromethylated aromatic compounds by direct trifluoromethylation with trifluoromethyl free radicals is known in the art. This process requires the use of such sources of trifluoromethyl radicals as hexafluoroacetone, trifluoromethyl copper or trifluoromethyl iodide. These reagents waste half of the radicals in forming fluoroform ($CF_3H$) and sometimes yield dihydroaromatic dimers as the major product. This process would inherently produce low isomeric selectivity whenever isomer formation is possible. Multiple trifluoromethylation is another problem unless a large excess of aromatic compound is utilized.

U.S. Pat. No. 2,273,992 discloses the process for preparing trifluoromethylnaphthalene utilizing such a free radical process by reacting carbon tetrachloride and anhydrous hydrogen fluoride in the presence of copper. The process disclosed in this patent utilizes a high temperature of 150°-155° C. for extended periods of time (48 hours). Moreover the disclosure in this patent reports the formation of an unspecified amount of by-product containing 41.5% fluorine which is probably $C_{20}H_{12-16}(CF_3)_4$ resulting from multiple trifluoromethylation and dimerization reactions typical of free radical trifluoromethylations. Cupric fluoride, a possible product of the reaction of copper metal, carbon tetrachloride, and hydrogen fluoride under the conditions of this patent, is a base in liquid hydrogen fluoride.

Trifluoromethylation via coupling of aryl iodides with trifluoromethyl radicals or trifluoromethyl copper reagents reduces the wastage due to formation of $CF_3H$. This known process permits isomeric selectivity but requires a troublesome synthesis of the appropriate aryl iodide and recycling of the iodide released. The production of the trifluoromethyl radicals still requires the difficultly obtainable (on a commercial scale) trifluoroacetic acid or trifluoromethyl iodide.

Conversion of carboxyl groups to trifluoromethyl groups is also reported in the literature. However, this process utilizes toxic, expensive and difficultly recycleable reagents such as sulfur tetrafluoride, molybdenum hexafluoride or tungsten pentafluoride. Large quantities of such reagents are required because they, not anhydrous hydrogen fluoride, are the source of fluorine for the conversion.

The most widely utilized process for the preparation of trifluoromethylated aromatic compounds involves the chloride-fluoride exchange reaction using acidic fluorides or hydrogen fluoride as the fluoride source. This reaction is used to produce fluorinated hydrocarbons as well as benzotrifluorides. The reaction can be run without a catalyst at high temperatures but in commercial practice a catalyst such as $FeCl_3$ or $SbCl_2F_3$ is utilized. This process uses readily available raw materials except when an unusual isomer of a methylated aromatic compound is required but takes at least two steps and suffers from corrosion and condensation problems during the exchange step. The chlorination and exchange steps of the process have not been combined because the catalyst for the exchange step also catalyzes nuclear chlorination and because corrosion problems are more difficult to solve when the properties of chlorine are combined with those of hydrogen fluoride - hydrogen chloride mixtures.

SUMMARY OF THE INVENTION

This invention relates to the preparation of monotrifluoromethylated aromatic compounds which comprises reacting an aryl or substituted aryl compound with carbon tetrahalide and hydrogen fluoride in the presence of a strong Bronsted or Lewis acid which gives an acidic reaction (increase in concentration of $H_2F^+$ ions) at temperatures from about −20° C. to about 300° C. under pressures from about atmospheric pressure to about 3,000 psig and in which the catalyst to carbon tetrahalide to aromatic compound to hydrogen chloride molar ratios are in the range of from about 0.01/0.2/1.0/0.6 to about 5/10/1/100. Typical acidic catalysts which can be utilized in the process include antimony trichloride, antimony trifluoride, antimony pentachloride, antimony pentafluoride, titanium tetrachloride, titanium tetrafluoride, niobium pentachloride, niobium pentafluoride, tantalum pentachloride, tantalum pentafluoride or mixtures thereof.

Aromatic compounds which can be utilized in the process of this invention include benzene or those moderately deactivated benzene derivatives which are inert to anhydrous hydrogen fluoride. Typical deactivated benzene derivatives are those containing unsubstituted positions having a reactivity equivalent to a Hammett sigma value of 0 to +0.8, as disclosed in Corwin Hansch's article in Journal of Medicinal Chemistry Vol. 16, No. 11, pg 1209 to 1212, 1973.

DETAILED DESCRIPTION OF THE INVENTION

The direct trifluoromethylation process of this invention possesses particular advantages compared to other trifluoromethylation processes, Friedel-Crafts trihalomethylations and chloride-fluoride exchange reactions. In particular, liquid-phase Friedel-Crafts condensations of aromatic compounds with carbon tetrachloride result only in the formation of diaryl and triaryl methanes usually isolated as diaryl ketones and triaryl carbanols in the presence of steric factors inhibiting multiple arylation. The presence of hydrogen fluoride permits the trapping of a substantial portion of these intermediates as trifluoromethylated aromatic compounds. The choice of the strong acid catalysts of the present invention can be optimized to minimize the formation of multiple arylated products.

Carbon tetrachloride and anhydrous hydrogen fluoride are inexpensive large volume industrial chemicals used in the production of chlorofluoromethanes. The preferred catalysts for the direct trifluoromethylation process of the present invention, titanium tetrachloride and antimony pentachloride, are also readily available materials. When liquid hydrogen fluoride is present, those acidic catalysts such as titanium tetrachloride which are not inactivated by side-reactions with the substrate can be recycled by a mere phase separation. The hexafluoroacetone, trifluoromethyl iodide and trifluoroacetic acid reagents used in other direct trifluoromethylation procedures are not readily available materials which contributes to their high cost.

The single-step trifluoromethylation process of this invention eliminates or reduces the yield losses, the complexity in handling and the corrosion problems associated with the three-step chloride-fluoride exchange process: namely, synthesis of the appropriate methylarene, free radical chlorination to a trichloromethylated aromatic compound, and chloride-fluoride exchange. Moreover there is no need for a photochemical reaction and no problem of catalyst or by-product incompatibility as in the second or third steps of the chloride-fluoride exchange process.

The temperatures, pressures, and other conditions utilized in the process of this invention are similar to those used in the production of benzotrifluorides by chloride-fluoride exchange so that no large increase in the cost or complexity of equipment is required.

By contrast, the only other reported direct trifluoromethylation utilizing hydrogen fluoride and carbon tetrachloride, (U.S. Pat. No. 2,273,922, discussed above), requires 48 hours at 150°–155° C., both a higher temperature and a much longer time than this invention requires. Higher temperatures and low pressures can optionally be used in the present invention with the less volatile acid catalysts to permit a continuous, gas phase, hot tube, direct trifluoromethylation which can reduce still further the multiple arylation problem. The process reported in U.S. Pat. No. 2,273,922 is too slow to permit such an option.

Production of a by-product containing 41.5% fluorine corresponding approximately to the formula $C_{10}H_6(CF_3)_2$ (43.2% fluorine) but having a molecular weight above 500 is reported in U.S. Pat. No. 2,273,922. This patent did not specify the yields of trifluoromethylnaphthalene or the by-product containing 41.5% fluorine. Multiple trifluoromethylation is also a problem in direct trifluoromethylations which proceed by a free radical process.

The acid catalyzed direct trifluoromethylation of the present invention gives an electrophilic reactivity pattern such that introduction of the first trifluoromethyl group inhibits further trifluoromethylation. Such inhibition would be greatest for already deactivated benzene derivatives.

The process of this invention provides a method for the formation of isomers which cannot be easily obtained by any of the literature processes. For example, 2,5-dichlorobenzotrifluoride can be obtained much more readily by the reaction of p-dichlorobenzene with carbon tetrachloride and hydrogen fluoride with an acidic catalyst than it can be obtained by chlorination of benzotrifluoride or by other routes.

At best the acid catalyzed direct trifluoromethylation of aromatic compounds using hydrogen fluoride and carbon tetrachloride offers major advantages over the prior art by permitting use of readily available raw materials, process simplification, moderation of reaction conditions, reduction of by-product formation and providing a simple route to unusual isomers. This process has the additional advantage of producing as a co-product chlorofluoromethanes (primarily $CFCl_3$) a commercial product. The process will be particularly advantageous for making compounds where electrophilic substitution isomers cannot be formed.

Aromatic compounds which can be utilized in the process of the present invention include all aromatic compounds possessing at least one unsubstituted position including benzene, naphthalene and polycyclic aromatic compounds derivatives and polymers containing same. However, aromatic compounds having a reactivity equivalent to a Hammett sigma value of 0 to +0.8 and which are inert to anhyrous hydrogen fluoride are preferred. Hammet sigma values are strictly undefined for ortho-substituents (e.g., a reaction involving a p-disubstituted benzene such as p-dichlorobenzene) and poorly defined for aromatic compounds other than benzene derivatives. However "a reactivity equivalent to a Hammet sigma value of 0 to +0.8" can be determined by a comparison of other reactions of the compound with those of the benzene derivatives for which sigma constants are defined.

Typical aromatic compounds encompassed by this invention include: benzene, halobenzene, dihalobenzenes such as o-dichlorobenzene, p-dichlorobenzene or m-dichlorobenzene, toluene, monohalotoluenes, except fluorotoluene, such as p-chlorotoluene, o-chlorotoluene or m-chlorotoluene, dihalotoluenes such as o-dichlorotoluene or o-dibromotoluene, benzoic acid, acetophenone, nitrobenzene, nitrotoluenes, phenylacetic acid, azobenzene, benzenethiol, thioanisole, phenyl methyl sulfone, diphenyl sulfide, o-chloroanisole, p-chloroanisole, o-nitroanisole, p-chloroanisole, diphenyl sulfone, phenyldifluorophosphine, phenyltrifluorosilane, cinnamic acid, benzonitrile, biphenyl, naphthalene, 1- or 2-nitronaphthalene, mono-, di- or trichloronaphthalenes, triphenylphosphine, phenyldimethylphosphine, phenylmercuric chloride, ferrocene and polystyrene. Phenylmercuric chloride and ferrocene represent the class of organometallic compounds with aromatic reactivity patterns and relatively high stability to acids; polystyrene represents the class of polymers containing pendant aromatic groups.

The preferred aromatic compound encompassed by this invention are those having a reactivity equivalent to a Hammet sigma value of 0 to +0.8 and which are inert to anhydrous hydrogen fluoride. These include: benzene, chlorobenzene, fluorobenzene, bromobenzene, iodobenzene, dihalobenzenes, such as o-dichlorobenzene, p-dichlorobenzene or m-dichlorobenzene, mono- and dihalotoluenes except fluorotoluenes, benzoic acid, acetophenone, nitrobenzene, mononitrotoluenes, phenylacetic acid, azobenzene, benzenethiol, thioanisole, phenyl methyl sulfone, diphenyl sulfide, o-chloroanisole, o-nitroanisole, diphenyl sulfone, diphenyl sulfide, phenyldifluorophosphine, p-chloroanisole, p-nitroanisole, diphenyl sulfone, phenyldifluorophosphine, phenyltrifluorosilane, cinnamic acid, and 1- or 2-nitronaphthalenes. The most preferred aromatic compounds encompassed by this invention include chlorobenzene, o-dichlorobenzene, p-dichlorobenzene, m-dichlorobenzene, all other mono- and dihalobenzenes, and all mono- and dihalotoluenes except fluorotoluenes. Carbon tetrahalides which can be utilized in the process of this invention include carbon tetrachloride, carbon tetrabromide, chlorotrifluoromethane and other such carbon tetrahalides having the formula $CCl_xBr_{4-x}$ or $CCl_xF_{4-x}$ where x is an integer from 1 to 3. A preferred carbon tetrahalide of this invention is carbon tetrachloride.

Acid catalysts which may be utilized in this invention include any strong Bronsted or Lewis acid which gives an acidic reaction (increase in concentration of $H_2F^+$) in anhydrous hydrogen chloride as measured by $H_o$ or similar acidity scales or by enhanced solubility of xylenes or other basic aromatic hydrocarbons in anhydrous hydrogen fluoride. Bronsted acids are proton doners such as $HSO_3Cl$, $HSO_3F$ and $HSbF_6$. Lewis acids are electron pair acceptors such as SbF$_5$, TiF$_4$, TiCl$_4$, TaF$_5$, AsF$_5$, and phenyl antimony tetrafluoride. Excluded are weaker Bronsted and Lewis acids such as nitric, sulfuric, hydrochloride, cupric chloride, zinc fluoride and ferric fluoride which are not acids in hydrogen fluoride. The class of strong acids utilized in the present invention include fluorides, chlorides and other salts of elements of Groups 4B to 6B of the transition metal series and 3A to 5A of the main group of elements of the Periodic Table and mixtures of these salts. The preferred catalysts are titanium tetrachloride or tetrafluoride, antimony (III) and (V) fluorides, chlorofluorides and chlorides alone or mixed and niobium and tantalum pentachlorides or pentafluorides or mixtures of the above.

The process of the present invention can be performed at temperatures from about −20° C. to about 300° C. preferably from about 0° C. to about 130° C. The temperature range utilized is catalyst dependent. Temperatures of over 150° C. can only be used at low pressures during gas phase reactions.

Pressures which can be utilized in the process of this invention range from about 10 millimeters to about 3,000 pounds psig. preferably from about 1 atmosphere to about 750 psig. Although the process of this invention is preferably conducted under conditions of temperature and pressure such that liquid hydrogen fluoride is present during the reaction, high temperature trifluoromethylation with all of the components except the catalyst in the vapor phase in a tube type reactor can also be utilized if a less volatile and less reactive catalyst such as titanium tetrafluoride or aluminum fluoride is utilized.

The process of this invention is preferably run from about 1 minute to about 24 hours more preferably from about 30 minutes to 4 hours then depending upon the reactivity of the catalyst.

The process of this invention can be run either as a batch process or as a continuous process using CFSTR, (continuous flow stirred tank reactor), hot tube, loop or co-current packed bed reactors. In all processes the recycle of catalyst, hydrogen fluoride, unconverted aromatic compound and carbon tetrahalide can be utilized to optimize efficient productivity.

The range of catalysts to carbon tetrahalide to aromatic compounds to hydrogen fluoride molar ratios which can be utilized in the present invention are from about 0.01/0.2/1.0/0.6 to about 5/10/1/100 in particular from about 0.1/0.5/1.0/2.0 to about 1/2/1/20.

The following examples are presented merely to illustrate the process of this invention. These examples are not to be construed in any way as defining the metes and bounds of this invention.

EXAMPLE 1

14.7 g of o-dichlorobenzene and 23.2 of carbon tetrachloride were charged to an unpressurized 500 ml polypropylene reaction vessel cooled to −78° C. and containing 20 ml of anhydrous hydrogen fluoride, 10.7 g of antimony pentafluoride and a magnetic stirrer. The mixture was warmed to 0° C. and allowed to react with stirring for four hours. A plastic condenser cooled to −20 C. was used to minimize the loss of hydrogen fluoride in the stream of hydrogen chloride evolved during the reaction. After cooling the deep red brown inhomogeneous reaction mixture was quenched with 50 ml of deionized water, neutralized with 7.5 N aqueous potassium hydroxide, and extracted with several 15 ml portions of methylene chloride. Internal standard glpc analysis of the filtered extract gave the following yields: 4.2 g dichlorobenzotrifluoride (DCBTF) isomers, 2.0 g trichlorobenzenes, and 2.8 g recovered o-dichlorobenzene. Other products included fluorotrichloromethane and 5.8 g of impure tetrachlorobenzophenone. The weight of the latter was obtained by evaporation of an aliquot of the extract.

EXAMPLE 2

10–12 ml of anhydrous hydrogen fluoride was condensed in an unpressured 500 ml polypropylene reaction vessel cooled to −78° C. and containing 12.3 g of antimony pentafluoride and a magnetic stirrer. The reaction vessel was warmed to 0° C., stirring was initiated, and a mixture containing 77.8 g of o-dichlorobenzene and 172.1 g of carbon tetrachloride (31.1 weight percent o-dichlorobenzene) was continuously added for 4 hours and 35 minutes at a rate of 0.1628 gram/minute. (This corresponds to 13.9 g of o-dichlorobenzene and 30.8 g of carbon tetrachloride.)

A plastic condenser cooled to −10° to −15° C. was used to minimize the loss of hydrogen fluoride in the stream of hydrogen chloride and difluorodichloromethane evolved from the reaction mixture. After 5 additional minutes the reaction mixture was cooled, quenched with 50 ml deionized water, neutralized with 7.5 N aqueous potassium hydroxide and extracted with several 15 ml portions of methylene chloride. Internal standard glpc analysis of the filtered extract gave the following yields: 5.0 g DCBTF isomers, 1.13 g trichlorobenenes, 0.75 g 1,2,4,5-tetrachlorobenzene, and 5.1 g recovered o-dichlorobenzene. Other products included fluorotrichloromethane, difluorodichloromethane and 5.2 g of impure tetrachlorobenzophenone. The weight of the latter was obtained by evaporation of an aliquot of the extract.

EXAMPLE 3

13.6 g of o-dichlorobenzene, 23.1 g of carbon tetrachloride and 9.1 g of titanium tetrachloride catalyst were added to a nitrogen-flushed 250 ml Berghof teflon-lined 316 stainless steel autoclave equipped with Monel gauges, valves and connectors, and a magnetic stirring bar. The autoclave was cooled in a dry ice—ethanol bath and 25 ml of hydrogen fluoride was distilled into the autoclave from a plastic vessel. The autoclave inlet and outlet values were closed, stirring was initiated and the autoclave was warmed to an internal temperature of 110°–116° C. Over a 90 minute reaction period the internal pressure increased from 100–580 psig. The autoclave was cooled to 0° C. and vented through a caustic scrubber. Then it was placed in a dry ice—ethanol bath and the reaction mixture was quenched with 40 ml of deionized water and neutralized with 7.5 N aqueous potassium hydroxide. The reaction quenched mixture was extracted with several 15 ml portions of methylene chloride. Internal standard glpc analysis of the filtered extract gave the following yields: 6.4 g DCBTF isomers and 2.1 g recovered o-dichlorobenzene. Other products include fluorotrichloromethane, a small amount of difluorodichloromethane and 6.5 g of an oily mixture containing tetrachlorobenzophenone and a probable hexachlorodiarylmethane. The weight of the latter was obtained by evaporation on an aliquot of the extract.

Table I below depicts other examples of the trifluoromethylation process of this invention. These examples show the preparation of dichlorobenzotrifluoride (DCBTF) by the direct trifluoromethylation of o-dichlorobenzene (DCB).

vented through a caustic scrubber. Then it was placed in a dry ice—acetone bath and the reaction mixture was

TABLE I

Preparation of Dichlorobenzotrifluoride Isomers by Trifluoromethylation of o-Dichlorobenzene[a]

| Ex. Number | o-DCB | Reactants (g)[c] Catalyst | CCl$_4$ | HF[b] | Reaction Conditions | Yield of DCBTF Isomers | Yields of Other Products |
|---|---|---|---|---|---|---|---|
| 4 | 14.7 | 3.8 SbCl$_5$ | 23.0 CCl$_4$ | 25 ml | 53 min at b.p. 20 min w/o HF (bath 17°C.) 1 atm - no condensor | 1.94 g | 0.84g 1,2,4-tri-chlorobenzene 9.2g recovered o-DCB 0.94g tetra-chlorobenzophenone, CFCl$_3$ |
| 5 | 14.8 | 5.7 TiF$_4$ | 49.5 CBr$_4$ | 24 g | 1.5 hr at 113°-115° C. 0-195 psig | 2.7 g | 7.4 recovered o-DCB, 2.31 g tetrachloro-benzophenone, unknowns |
| 6 | 14.8 | 10.4 g SbF$_5$ | 15.9 CFCl$_3$ | 10 ml | 4 hr at 0° C. 1 atm (condensor at −78° C.) | 0.25 g | 7.8 g recovered o-DCB 1.54 g trichloro-benzenes, 4.98 g of oily residue including tetrachloro-benzophenone |
| 7 | 14.9 | 12.2 TaF$_5$ add 2.2 SbF$_5$ | 23.3 CCl$_4$ | 10 ml | 21 hr at 0° C.; 2 hr at 17° C. 4.8 hr at 0° C.; 2 hr at 17° C. all at 1 atm | 0.49 g 1.51 g | 7.0 g oily residue, including tetrachloro-benzophenone 3.15 g recovered o-DCB, 9.0 g viscous oil containing tetra-chlorobenzophenone, CFCl$_3$ |
| 8 | 14.7 | 8.9 NbF$_5$ | 23.1 CCl$_4$ | 6–8 ml | 2.75 hr at 0° C. 3 hr at 17°-20° C,. 17 hr at 20°-25° C. most HF distilled during first hour at 20°-25° C. | 0.46 g | 5.9 g recovered o-DCB, 0.176 g trichloro-benzenes 6.1 g unknown oily residue |

[a] o-DCB is o-dichlorobenzene, DCBTF is dichlorobenzotrifluoride
[b] Added last by condensation
[c] In examples 6, 7 and 8 the polypropylene reactor was cooled to −78° C. before any reagents were added other than the catalyst.

EXAMPLE 9

11.3 g of chlorobenzene, 23.2 g of carbon tetrachloride and 9.6 g of titanium tetrachloride catalyst were added to a nitrogen-flushed 250 ml Berghof teflon-lined 316 stainless steel autoclave equipped with Monel gauges, values and connectors, and a magnetic stirring bar. The autoclave was cooled in a dry ice—acetone bath and 21.4 g of anhydrous hydrogen fluoride was added. The bomb was warmed to 0° C. with stirring and vented to remove the hydrogen chloride generated by the reaction of hydrogen fluoride with the catalyst. The valves were closed, and the autoclave was heated to an internal temperature of 91°-102° C. Over a 2.5 hour reaction period the internal pressure increased from 50 to 295 psig. The autoclave was cooled to 0° C. and quenched with 40 ml of deionized water and neutralized with 7.5 N aqueous potassium hydroxide. The quenched reaction mixture was extracted with several 15 ml portions of methylene chloride. Internal standard glpc analysis of the filtered extract gave the following yields: 1.17 g chlorobenzotrifluoride isomers and 3.4 g recovered chlorobenzene. Other products included 4.1 g fluorotrichloromethane and 6.3 g of an oily residue containing dichlorobenzophenones. The weight of the latter was obtained by evaporation of an aliquot of the extract.

Table II below demonstrates that other aromatic compounds can be trifluoromethylated. The procedure of Example 1 was used for Examples 10 and 11 and the procedure of Example 9 was used for Example 12.

TABLE II

Trifluoromethylation of Other Aromatic Compounds

| Ex. No. | Reactants (g) Aromatic Compounds | Catalyst | CCl$_4$ | HF | Reaction Conditions | Yield of Trifluoro-methylation Product | Yields of Other Products |
|---|---|---|---|---|---|---|---|
| 10 | 11.2 chloro-benzene | 2.8 SbCl$_5$ | 23.4 | 35 ml | 5.3 hr at 17°-22° C. 1 atm | less than 0.002 g chloroben-zo-trifluorides | 0.63 g dichloro-benzenes 0.16 g dichloro-benzophenone no fluorotri-chloromethane |

TABLE II-continued
Trifluoromethylation of Other Aromatic Compounds

| Ex. No. | Reactants (g) Aromatic Compounds | Catalyst | CCl₄ | HF | Reaction Conditions | Yield of Trifluoromethylation Product | Yields of Other Products |
|---|---|---|---|---|---|---|---|
| 11 | 14.6 o-dichlorobenzene  11.3 chlorobenzene | 10.2 SbF₅ | 30.8 | 10 ml | 4 hr at 0° C. 1 atm | 0.21 g chlorobenzotrifluorides, no dichlorobenzotrifluorides | 3.5 g recovered chlorobenzene  12.0 g recovered o-dichlorobenzene  0.79 g p-dichlorobenzene  0.25 g 1,2,4-trichlorobenzene  7.8 g solid residue containing dichlorobenzophenone  0.25 g fluorotrichloromethane |
| 12 | 8.0 benzene | 10.7 TiCl₄ | 23.0 | 16 g | 1.5 hr at 96°–101° C. 50–250 psig | 0.190 g benzotrifluoride | 1.48 g recovered benzene  0.84 g benzophenone  5.0 g triphenylmethanol  0.88 g fluorotrichloromethane |
| 13 | 16.8 phenyl ether (PE) | 13.0 TiF₄ | 23.3 | 25 g | 50 min. at 104°–108° C.  50 290 psig | none | 3.6 g recovered phenyl ether  12.7 g of brown glass having empirical formula (PE) 1.0 (COH) 0.277 (CO) 0.11 (H) 1.05  0.026 g fluorotrichloromethane |

Obvious modifications of the process of this invention as described herein are meant to be encompassed by the following claims appended hereto.

I claim:

1. A process for the preparation of mono-trifluoromethylated aromatic compounds which comprises reacting an aromatic comound with carbon tetrahalide in the presence of a strong Bronsted or Lewis acid in anhydrous hydrogen fluoride at temperatures from about −20° C. to about 300° C. under pressures from about 10 millimeters to about 3,000 psig wherein the catalyst to carbon tetrahalide to aromatic compound to hydrogen fluoride molar ratios are in the range of from about 0.01/0.2/1.0/0.6 to about 5/10/1/100.

2. A process according to claim 1 wherein the aromatic compound utilized is selected from the group consisting of benzene, naphthalene, polycyclic aromatic hydrocarbons, derivatives thereof and polymers containing same such that the unsubstituted position of the aromatic compound has a reactivity equivalent to a Hammett sigma values of 0 to +0.8 and the compound is inert to anhydrous hydrogen fluoride.

3. Process according to claim 2 wherein the aromatic compound is benzene or a deactivated benzene derivative which is inert to anhydrous hydrogen fluoride containing unsubstituted positions having a reactivity equivalent to a Hammett sigma value of 0 to +0.8.

4. A process according to claim 3 wherein the catalyst is selected from the class of strong acids selected from fluorides and chlorides of elements of groups 4B to 6B and 3A to 5A of the Periodic Table and mixtures thereof.

5. The process according to claim 4 wherein the catalysts are selected from antimony trichloride, antimony trifluoride, antimony pentachloride, antimony pentafluoride, titanium tetrachloride, titanium tetrafluoride, niobium pentachloride, niobium pentafluoride, tantalum pentachloride, tantalum pentafluoride and mixtures thereof.

6. A process according to claim 5 wherein the reaction is carried out in a batch process.

7. A process according to claim 5 wherein the process is carried out in a continuous process.

8. A process according to claim 5 wherein the range of catalyst to carbon tetrahalide to aromatic compound to hydrogen fluoride molar ratios are from about 0.1/0.5/1.0/2.0 to about 1/2/1/20.

9. A process according to claim 8 wherein the reaction is run at pressures from about 1 atmosphere to about 750 psig.

10. A process according to claim 9 wherein the temperature utilized is in the range from about 0 to about 130° C.

11. A process according to claim 10 wherein the carbon tetrahalide has the formula $CCl_xBr_{4-x}$ or $CCl_yF_{4-y}$ wherein x is an integer from 0 to 4 and y is an integer from 1 to 4.

12. A process according to claim 11 wherein the carbon tetrahalide is carbon tetrachloride.

13. A process according to claim 12 wherein the aromatic compound utilized is selected from the group consisting of benzene, halobenzene, dihalobenzenes, mono- and dihalotoluenes except fluorotoluenes, benzoic acid, acetophenone, nitrobenzene, mononitrotoluenes, phenylacetic acid, azobenzene, benzenethiol, thioanisole, phenyl methyl sulfone, diphenyl sulfide, o-chloroanisole, o-nitroanisole, diphenyl sulfone, diphenyl sulfide, phenyldifluorophosphine, p-chloroanisole, p-nitroanisole, diphenyl sulfone, phenyldifluorophosphine, phenyltrifluorosilane, cinnamic acid, and 1- or 2-nitronaphthalenes.

14. A process according to claim 13 wherein the aromatic compound is selected from benzene mono- and dihalobenzenes, and all mono- and dihalotoluenes except monofluorotoluenes.

* * * * *